United States Patent [19]

Lunts

[11] Patent Number: 4,921,867
[45] Date of Patent: May 1, 1990

[54] PYRIDINE COMPOUNDS USEFUL FOR THERAPY OR PROPHYLAXIS OF A DISEASE ASSOCIATED WITH AIRWAY OBSTRUCTION

[75] Inventor: Lawrence H. C. Lunts, Broxbourne, England

[73] Assignee: Glaxo Group Limited, London, England

[21] Appl. No.: 153,938

[22] Filed: Feb. 9, 1988

[30] Foreign Application Priority Data

Feb. 10, 1987 [GB] United Kingdom ............... 8703007

[51] Int. Cl.⁵ .................... A61K 31/13; C07C 93/08
[52] U.S. Cl. .................... 514/345; 514/347; 514/348; 514/349; 514/350; 514/351; 514/352; 514/357; 546/293; 546/294; 546/296; 546/297; 546/298; 546/299; 546/300; 546/301; 546/334
[58] Field of Search ............... 546/293, 294, 296, 297, 546/298, 299, 300, 301, 334; 514/345, 347, 348, 349, 350, 351, 352, 357

[56] References Cited

U.S. PATENT DOCUMENTS 4,379,166  4/1983  Neustadt .................... 546/176

FOREIGN PATENT DOCUMENTS 0021636  1/1981  European Pat. Off. ............ 546/300
0220878  5/1987  European Pat. Off. ............ 546/334
3434271  3/1986  Fed. Rep. of Germany ...... 546/121
1178191  1/1970  United Kingdom ............... 546/334
1445740  3/1974  United Kingdom ............... 546/334
1599061  9/1981  United Kingdom ............... 546/176
2088873  6/1982  United Kingdom ............... 546/300

Primary Examiner—Mary C. Lee
Assistant Examiner—Zinna Northington-Davis

[57] ABSTRACT

Compounds of formula (I)

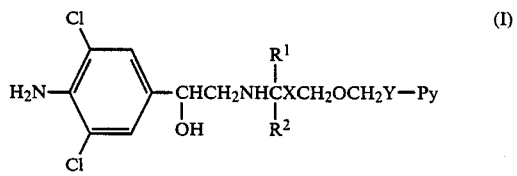

wherein

X and Y each represent a bond or an alkylene, alkenylene or alkynylene chain;

$R^1$ and $R^2$ each represent a hydrogen atom or a lower alkyl group; and

Py represents a pyridyl group having one or two substituents. The compounds have a stimulant action at beta₂-adrenoreceptors. The compounds may be used in the treatment of diseases associated with reversible airway obstruction such as asthma and chronic bronchitis.

9 Claims, No Drawings

PYRIDINE COMPOUNDS USEFUL FOR THERAPY OR PROPHYLAXIS OF A DISEASE ASSOCIATED WITH AIRWAY OBSTRUCTION

This invention relates to dichloroaniline derivatives having a stimulant action at $\beta_2$-adrenoreceptors, to processes for their preparation, to pharmaceutical compositions containing them and to their use in medicine.

Dihaloaniline derivatives have previously been described as bronchodilators having stimulant activity at $\beta$-adrenoreceptors.

Thus British Patent Specification No. 1178191 describes compounds of the general structure

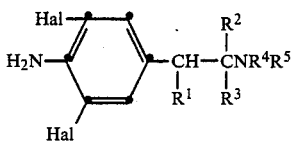

in which the substituents Hal represent bromine or chlorine atoms; $R^1$ represents hydrogen or hydroxyl; $R^2$ and $R^3$ each represent hydrogen or $C_{1-4}$ alkyl; and $R^4$ and $R^5$ each represent hydrogen, $C_{1-6}$ alkyl, alkenyl, alkynyl, hydroxyalkyl, alkoxyalkyl, dialkylaminoalkyl, cycloalkyl, phenyl, benzyl or adamantyl, or $NR^4R^5$ forms a heterocyclic ring optionally substituted by $C_{1-3}$ alkyl groups.

We have now found a novel group of dichloroaniline derivatives, which differ structurally from those described in British Patent Specification No. 1178191, and which have a desirable and useful profile of activity.

Thus the present invention provides compounds of the general formula (I)

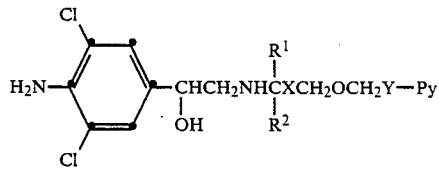

wherein

X represents a bond, or a $C_{1-6}$ alkylene, $C_{2-6}$ alkenylene or $C_{2-6}$ alkynylene chain, and Y represents a bond, or a $C_{1-6}$ alkylene, $C_{2-6}$ alkenylene or $C_{2-6}$ alkynylene chain with the proviso that the sum total of carbon atoms in X and Y is not more than 10;

$R^1$ and $R^2$ each represent a hydrogen atom or a $C_{1-3}$ alkyl group, with the proviso that the sum total of carbon atoms in $R^1$ and $R^2$ is not more than 4; and Py represents a pyridyl group substituted by one or two substituents selected from nitro, $-(CH_2)_tR^3$, $-NR^4R^5$, $-(CH_2)_rSO_{2L}$ $NR^4R^5$, $-NR^6COR^3$, $-NR^6SO_2R^7$, $-(CH_2)_rCOR^3$, $-OCH_2COR^3$ or $-O(CH_2)_qR^3$; where $R^3$ represents a hydroxy, $C_{1-3}$ alkoxy or $-NR^4R^5$ group;

$R^4$ and $R^5$ each represent a hydrogen atom or a $C_{1-4}$ alkyl group or $-NR^4R^5$ forms a saturated heterocyclic amino group which has 5-7 ring members and optionally contains in the ring one or more atoms selected from $-O-$ or $-S-$ or a group $-NH-$ or $-N(CH_3)-$;

$R^6$ represents a hydrogen atom or a $C_{1-4}$ alkyl group;

$R^7$ represents a $C_{1-4}$ alkyl, phenyl or $-NR^4R^5$ group;

q represents an integer 2 or 3;

r represents an integer from 0 to 3; and t represents an integer 1,2 or 3;

and physiologically acceptable salts and solvates (e.g. hydrates) thereof.

It will be appreciated that the compounds of general formula (I) possess one or two asymmetric carbon atoms, namely the carbon atom of the

group and, when $R^1$ and $R^2$ are different groups, the carbon atom to which these are attached. The compounds according to the invention thus include all enantiomers, diastereoisomers and mixtures thereof, including racemates. Compounds in which the carbon atom in the

group is in the R configuration are preferred.

In the definition of general formula (I), the term alkenylene includes both cis and trans structures.

According to one aspect, the invention provides compounds of formula (I) in which $R^1$, $R^2$ and X are as defined in formula (I), Y is a $C_{1-4}$alkylene, $C_{2-4}$alkenylene or $C_{2-4}$alkynylene chain, and Py is as defined in formula (I) with the proviso that Py does not represent a pyridyl group substituted by the group $-NR^6COR^3$.

In the general formula (I), the chain X may be for example a bond, $-CH_2-$, $-(CH_2)_2-$, $-(CH_2)_3-$, $-(CH_2)_4-$, $-(CH_2)_5-$, $-(CH_2)_6-$, $-CH_2C\equiv C-$, $-(CH_2)_2CH=CH-$, $-(CH_2)_2C\equiv C-$, $-CH=CHCH_2-$, $-CH=CH(CH_2)_2-$ or $-CH_2C\equiv CCH_2-$. The chain Y may be for example a bond, $-CH_2-$, $-(CH_2)_2-$, $-(CH_2)_3-$, $-(CH_2)_4-$, $-(CH_2)_5-$, $-CH=CH_{13}$, $-C\equiv C-$, $-CH_2CH=CH-$ or $-CH_2C\equiv C-$.

In one preferred group of compounds of formula (I) X represents a $C_{2-6}$ alkynylene or, more preferably, a $C_{1-6}$ alkylene chain and Y represents a $C_{1-6}$ alkylene chain.

Preferably the total number of carbon atoms in the chains X and Y is 4 to 9 inclusive. Particular compounds of this type are those wherein X is $-(CH_2)_3-$ or $-(CH_2)_4-$ and Y is $-CH_2-$, $-(CH_2)_2-$, $-(CH_2)_3-$, or $(CH_2)_5-$ or X is $-(CH_2)_2C\equiv C-$ and Y is $-(CH_2)_2-$.

In the compounds of formula (I) $R^1$ and $R^2$ may each be, for example, methyl, ethyl, propyl or isopropyl groups except that if one of $R^1$ and $R^2$ is a propyl or isopropyl group, the other is a hydrogen atom or a methyl group. $R^1$ and $R^2$ are each preferably a hydrogen atom or a methyl group.

A preferred group of compounds are those wherein $R^1$ and $R^2$ are both hydrogen atoms, or $R^1$ is a hydrogen atom and $R^2$ is a $C_{1-3}$ alkyl group, particularly a methyl group.

The pyridyl group represented by Py may be attached to the rest of the molecule at either the 2-, 3- or 4-position. The substituent(s) in the pyridyl ring may be at the 2, 3-, 4-, 5- or 6-position(s).

When —NR$^4$R$^5$ represents a saturated heterocyclic amino group, this may contain 5, 6 or 7 ring members and may be, for example, a pyrrolidino, piperidino, hexamethyleneimino, piperazine, N-methylpiperazino, morpholino, homomorpholino or thiamorpholino group.

Py may be for example a pyridyl group substituted by nitro; amino; diC$_{1-4}$alkylamino (e.g. dimethylamino); —(CH$_2$)$_r$COR$^3$ where r is an integer from 0 to 3 (e.g. 0 or 1) and R$^3$ is a hydroxy, C$_{1-3}$alkoxy (e.g. methoxy or ethoxy), amino or diC$_{1-4}$alkylamino (e.g. diethylamino) group; —(CH$_2$)$_r$SO$_2$NR$^4$R$^5$ where r is an integer from 0 to 3 (e.g. 0) and R$^4$ and R$^5$ are C$_{1-4}$alkyl (e.g. ethyl) groups; —NR$^6$COR$^3$ where R$^6$ is a hydrogen atom and R$^3$ is a C$_{1-4}$alkyl (e.g. methyl) group; —NR$^6$SO$_2$R$^7$ where R$^6$ is a hydrogen atom, and R$^7$ is a C$_{1-4}$alkyl (e.g. methyl) group; —(CH$_2$)$_t$R$^3$ and t is an integer from 1 to 3 (e.g. 2) and R$^3$ is a hydroxy group; —OCH$_2$COR$^3$ where R$^3$ is a diC$_{1-4}$alkylamino (e.g. diethylamino) or C$_{1-3}$alkoxy (e.g. methoxy) group; or —O(CH$_2$)$_q$R$^3$ where q is an integer 2 or 3 (e.g. 2) and R$^3$ is a hydroxy group.

Particularly preferred examples of the group Py include a pyridyl group substituted by nitro, amino; dimethylamino; —(CH$_2$)$_r$—COR$^3$ where r is 0 or 1 and R$^3$ is C$_{1-3}$ alkoxy (e.g. methoxy or ethoxy), amino or dimethylamino; —SO$_2$N(C$_2$H$_5$)$_2$; —NHCOCH$_3$; —OCH$_2$COR$^3$ where R$^3$ is —N(C$_2$H$_5$)$_2$ or —OCH$_3$; or —OCH$_2$CH$_2$OH. Preferably the pyridyl group is attached to the rest of the molecule via the 2 or 3 position and the substituents are at the 3, 4, 5 or 6 position.

A particularly preferred group of compounds according to the invention are those of formula (I) wherein R$^1$ represents a hydrogen atom and R$^2$ represents a methyl group or more preferably a hydrogen atom; the groups X and Y are both alkylene chains in which X is a C$_4$ alkylene chain and Y is a methylene, ethylene or pentylene chain; and Py represents a pyridyl group, attached to the rest of the molecule via the 2 or 3 position, and substituted by nitro; amino; dimethylamino, —(CH$_2$)$_r$COR$^3$ (where r is 0 or 1 and R$^3$ is methoxy, ethoxy, amino or dimethylamino), —SO$_2$N(C$_2$H$_5$)$_2$; —NHCOCH$_3$, —OCH$_2$COR$^3$ (where R$^3$ is —N(C$_2$H$_5$)$_2$ or methoxy), or —OCH$_2$CH$_2$OH, which are at the 3, 4, 5 or 6 position.

Preferred compounds according to the invention are:
methyl 5-[3-[[6-[[2-(4-amino-3,5-dichlorophenyl)-2-hydroxyethyl]amino]hexyl]oxy]propyl]-3-pyridinecarboxylate;
2-[3-[[6-[[2-(4-amino-3,5-dichlorophenyl)-2-hydroxyethyl]amino]hexyl]oxy]propyl]-4-pyridinecarboxamide;
N-[6-[3-[[6-[[2-(4-amino-3,5-dichlorophenyl)-2-hydroxyethyl]amino]hexyl]oxy]propyl]-2-pyridinyl]methanesulphonamide;
2-[6-[[6-[[2-(4-amino-3,5-dichlorophenyl)-2-hydroxyethyl]amino]hexyl]oxy]hexyl]-4-pyridinecarboxamide.
and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, tricarballylates, hydroxy-naphthalenecarboxylates e.g. 1-hydroxy- or 3-hydroxy-2-naphthalenecarboxylates including 4,4' methylenebis(3-hydroxy-2-naphthalenecarboxylic acid), or oleates. The compounds may also form salts with suitable bases where appropriate. Examples of such salts are alkali metal (e.g. sodium and potassium), and alkaline earth metal (e.g. calcium or magnesium) salts.

The compounds according to the invention have a stimulant action at $\beta_2$-adrenoreceptors, which furthermore is of a particularly advantageous profile. The stimulant action was demonstrated in the isolated trachea of the guinea-pig, where compunds were shown to cause relaxation of contractions induced by PGF$_{2\alpha}$ or electrical stimulation. Compounds according to the invention have shown a particularly long duration of action in these tests.

The compounds according to the invention may be used in the treatment of diseases associated with reversible airways obstruction such as asthma and chronic bronchitis.

The compounds according to the invention are also indicated as useful for the treatment of inflammatory and allergic skin diseases, congestive heart failure, depression, premature labour, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges or e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes. In the following description, X, Y, Py, $R^1$ and $R^2$ are as defined for general formula (I) unless otherwise specified. In the preparation of both intermediates and end-products the final step in the reaction may be the removal of a protecting group. Suitable protecting groups and their removal are described in general process (3) below.

In one process (1) compounds of formula (I) may be prepared by reducing an intermediate of general formula (II):

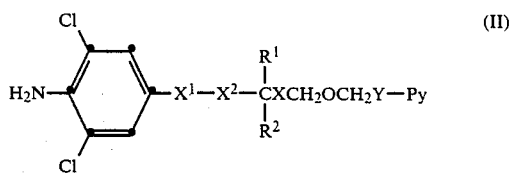

(II)

wherein at least one of $X^1$, $X^2$, X and Y represents a reducible group and the other(s) take the appropriate meaning as follows, which is $X^1$ is —CH(OH)—, $X^2$ is —CH$_2$NR$^8$— (where $R^8$ represents a hydrogen atom or a protecting group), and X and Y are as defined in formula (I), followed where necessary by removal of any protecting groups.

Suitable reducible groups include those wherein $X^1$ is a group >C=O, $X^2$ is a group —CH$_2$NR$^9$— (wherein $R^9$ represnts a group convertible to hydrogen by catalytic hydrogenation, for example an arylmethyl group such as benzyl, benzhydryl or α-methylbenzyl), X is $C_{2-6}$ alkenylene or alkynylene, and Y is $C_{2-6}$ alkenylene or alkynylene.

The reduction may be effected using reducing agents conveniently employed for the reduction of ketones, protected amines, alkenes and alkynes.

Thus, for example, when $X^1$ in general formula (II) represents a >C=O group this may be reduced to a —CH(OH)— group using hydrogen in the presence of a catalyst such as platinum, platinum oxide, palladium, palladium oxide, Raney nickel or rhodium, on a support such as charcoal, using an alcohol e.g. ethanol, an ester e.g. ethyl acetate, an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres. Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in a solvent, where appropriate an alcohol e.g. methanol or ethanol, an ether such as tetrahydrofuran, a halogenated hydrocarbon such as dichloromethane, a hydrocarbon such as benzene, or a mixture of one or more such solvents.

When $X^2$ in general formula (II) represents a —CH$_2$NR$^9$— group, X is a $C_{2-6}$ alkenylene or alkynylene group and/or Y is a $C_{2-6}$ alkenylene or alkynylene group, this may be reduced to a —CH$_2$NH—, $C_{2-6}$ alkylene or $C_{2-6}$ alkylene group respectively using hydrogen in the presence of a catalyst as described above.

Where it is desired to use a protected intermediate of general formula (II) it is particularly convenient to use a protecting group $R^8$ which is capable of being removed under the reducing conditions, for example hydrogen and a catalyst, thus avoiding the need for a separate deprotection step. Suitable protecting groups of this type include arylmethyl groups such as benzyl, benzhydryl and α-methylbenzyl.

In the above reduction process, and also in the preparation of intermediates, care must be taken to avoid the use of hydrogen and a catalyst when products are required in which X and/or Y represent alkenylene or alkynylene groups.

In another general process (2) compounds of formula (I), in which $R^1$ and $R^2$ each represent a hydrogen atom, may be prepared by alkylation of an amine of formula (III)

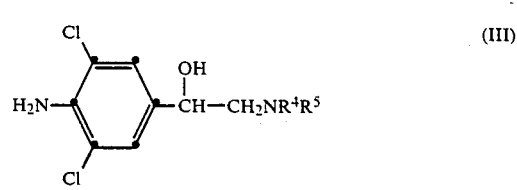

(III)

(wherein $R^4$ is a hydrogen atom or a protecting group and $R^5$ is a hydrogen atom) with a compound of formula (IV)

HalCH$_2$XCH$_2$OCH$_2$YPy     (IV)

(wherein X, Y and Py are as previously defined in formula (I), and Hal is a halogen atom, e.g. bromine) followed by removal of any protecting group where present.

The alkylation is preferably effected in the presence of a suitable acid scavenger, for example, inorganic bases such as sodium or potassium carbonate, organic bases such as triethylamine, N,N-diisopropylethylamine or pyridine, or alkylene oxides such as ethylene oxide. The reaction is conveniently effected in a solvent such as acetonitrile or an ether e.g. tetrahydrofuran or dioxan, a ketone e.g. acetone or butanone, a substituted amide e.g. dimethylformamide, a halogenated hydrocarbon e.g. chloroform, or a mixture of one or more such solvents, at a temperature between 0° and 100° C., for example, in the range 25° to 75° C.

In a further process (3) compounds of formula (I) may be prepared by deprotecting an intermediate of general formula (V)

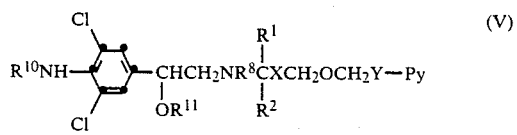

wherein $R^8$, $R^{10}$ and $R^{11}$ each represent a hydrogen atom or a protecting group with the proviso that at least one of $R^8$, $R^{10}$ and $R^{11}$ represents a protecting group.

The protecting group may be any conventional protecting group as described for example in "Protective Groups in Organic Synthesis", by Theodora Greene (John Wiley and Sons Inc, 1981). Thus hydroxyl groups may for example be protected by arylmethyl groups such as benzyl, diphenylmethyl or triphenylmethyl, by acyl groups such as acetyl, or as tetrahydropyranyl derivatives. Examples of suitable amino protecting groups include arylmethyl groups such as benzyl, α-methylbenzyl, diphenylmethyl or triphenylmethyl, and acyl groups such as acetyl, trichloroacetyl or trifluoroacetyl.

The deprotection to yield a compound of general formula (I) may be effected using conventional techniques. Thus for example arylmethyl grops may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with an acid such as a mineral acid e.g. hydrochloric acid, or a bas such as sodium hydroxide or potassium carbonate, and a group such as trichloroacetyl or trifluoracetyl may be removed by reduction with, for example, zinc and acetic acid.

Compounds of formula (I) may also be prepared by a process comprising interconversion of one compound of formula (I) into another.

Thus for example compounds of formula (I) in which Py represents a pyridyl group substituted by the group —(CH$_2$)$_r$COR$^3$ where $R^3$ is hydroxy may be prepared by hydrolysis of the corresponding compound of formula (I) in which $R^3$ represents C$_{1-3}$ alkoxy. The hydrolysis may for example be carried out under basic conditions using e.g. sodium hydroxide, in a solvent such as an alcohol e.g. ethanol or methanol, at normal or elevated temperature, for example from 15° to 100° C.

Intermediates of formula (II) for use in the reduction process (I) may be prepared by a number of processes, analogous to those described for the preparation of known compounds.

Thus for example intermediates of formula (II) in which Y is a C$_{2-6}$ alkynylene chain in which the acetylene group is adjacent to the group Py may be prepared by reaction of an intermediate of formula (VI) wherein 1$^1$ reprsents the group

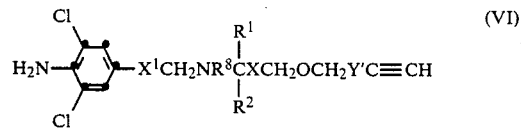

(wherein $R^8$ is a hydrogen atom or a protecting group and Y' is a bond or a C$_{1-4}$ alkylene chain) with a pyridyl halide, PyHal (where Hal is a halogen atom, e.g. bromine). The reaction may be carried out in the presence of a catalyst e.g. cuprous iodide, an organometallic reagent such as bis(triphenylphosphine)palladium (II) chloride and a base such as an organic amine e.g. diethylamine, triethylamine or dicyclohexylamine. The reaction may be effected in the presence of an additional solvent, where appropriate acetonitrile or an ether such as tetrahydrofuran, or a mixture of one or more such solvents.

Intermediates of formula (VI) in which $X^1$ represents the group

may be prepared by reaction of a haloketone of formula (VII)

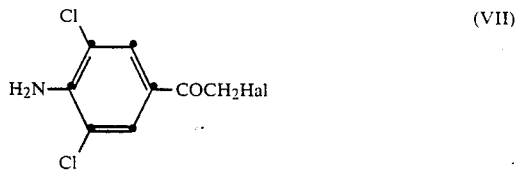

(where Hal represents a halogen atom e.g. bromine) with an amine of formula (VIII)

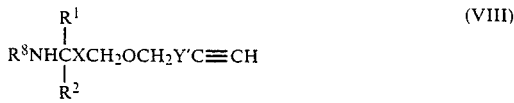

(where $R^8$ and Y' are as defined above). The reaction may be carried out in the presence of a base such as diisopropylethylamine in a solvent such as tetrahydrofuran.

Intermediates of formula (VI) wherein $X^1$ represents the group

may be prepared by reduction of the corresponding compound of formula (VI) in which $X^1$ represents the group

using a reducing agent such as sodium borohydride in a solvent such as an alcohol e.g. methanol.

Intermediates of formula (IV) for use in the alkylation process (2) may be prepared by a number of processes, analogous to those described for the preparation of known compounds.

Thus, for example, intermediates of formula (IV) in which Y is a $C_{2-6}$ alkynylene chain in which the acetylene group is adjacent to the group Py may be prepared by reaction of a compound of formula (IX)

$$HC\equiv CY'ch_2OCH_2XCH_2Hal \qquad (IX)$$

(wherein Y' is a bond or $C_{1-4}$ alkylene chain and Hal is as previously defined) with a pyridyl halide, PyHal where Hal is as defined above, using the general conditions as described above for preparing compounds of formula (II) from the compound of formula (VI).

Intermediates of formula (IX) may be prepared by the etherification reaction of a compound of formula (X).

$$HC\equiv CY'CH_2OH \qquad (X)$$

(wherein Y' is as previously defined) with a dihalo compound of the formula $HalCH_2XHal$, where Hal is as defined above.

The reaction is conveniently effected in the presence of an inorganic hydroxide such as sodium hydroxide, and a phase transfer catalyst such as tetrabutylammonium bisulphate, in an aqueous solvent. The reaction is preferably effected at a temperature in the range 0° to 100° C.

Intermediates of formula (IV) in which Y is a $C_{2-6}$ alkylene or $C_{2-6}$ alkenylene chain may be prepared by reduction of the corresponding compound of formula (IV) in which Y is a $C_{2-6}$ alkynylene chain. Thus compounds of formula (IV) in which Y is a $C_{2-6}$ alkylene chain may be prepared using hydrogen and a metal catalyst or a di-imide as the reducing agent.

Intermediates of formulae (VII), (VIII) and (IX) the pyridyl halides PyHal and the dihalides $HalCH_2XHal$ are either known compounds or may be prepared by methods analogous to those described for the preparation of known compounds. Suitable methods for preparing intermediates of formula (VIII) and the pyridyl halides PyHal are described in UK Patent Specification No. 2159151A and in the exemplification included hereinafter.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

In the following examples illustrate the invention. Temperatures are in °C. 'Dried' refers to drying using sodium sulphate. Thin layer chromatography (t.l.c.) was carried out on silica and flash column chromatography (FCC) was carried out on silica (Merck 9385). System A as used for chromatography denotes toluene:ethanol:triethylamine. The following abbreviations are used: THF-tetrahydrofuran, BTPC-bis(triphenylphosphine)palladium (II) chloride.

INTERMEDIATE 1 is
1-(4-Amino-3,5-dichlorophenyl)-2-bromoethanone

INTERMEDIATE 2

4-Amino-3,5-dichloro-α-[[(phenylmethyl)[6-[(2-propynyl)oxy]hexyl]amino]methyl]benzenemethanol A solution of Intermediate 1 (1.0 g), N-[6-[(2-propynyl)oxy]hexyl]benzenemethanamine (870 mg) and N,N-diisopropylethylamine (460 mg) in THF (10 ml) was left at room temperature for 25 min. The resulting precipitate was removed by filtration and the solvent was evaporated to leave a red oil which was dissolved in methanol (10 ml), cooled in an ice-bath, and treated portionwise with sodium borohydride (300 mg) under nitrogen. After the addition the yellow solution was stirred at room temperature for 1 h, then evaporated to an oil which was partitioned between water (25 ml) and ethyl acetate (25 ml). The aqueous layer was re-extracted with ethyl acetate (25 ml) and the combined organic extracts were washed with water and brine, dried and concentrated to a yellow oil which was purified by FCC eluting with hexane-ethyl acetate-trimethylamine (80:20:1) to give the title compound as a colourless oil (1.27 g), t.l.c. (Hexane-ethyl acetate-triethylamine 80:20:1) Rf 0.33.

INTERMEDIATE 3

2-[3-[[6-[[2-(4-Amino-3,5-dichlorophenyl)-2-hydroxyethyl](phenylmethyl)amino]hexyl]oxy]-1-propynyl]-4-pyridinecarboxamide A solution of 2-bromo-4-pyridinecarboxamide (1 g), Intermdiate 2 (2.2 g), BTPC (100 mg) and copper (I) iodide (10 mg) in diethylamine (10 ml) and acetonitrile (10 ml) was stirred under nitrogen overnight. The solution was concentrated in vacuo to give a brown oil which was purified by FCC eluting with System A (95:5:1) to give the title compound as a yellow oil (2 g), t.l.c. (System A 95:5:1) Rf 0.1.

INTERMEDIATE 4

Ethyl 2-[3-[[6-[[2-(4-amino-3,5-dichlorophenyl)-2-hydroxyethyl](phenylmethyl)amino]hexyl]oxy]-1-propynyl]-4-pyridinecarboxylate Ethyl 2-bromo-4-pyridinecarboxylate (2.1 g) and Intermediate 2 (4.14 g) were treated as in Intermediate 3 to give, after FCC eluting with System A (98:2:1), the title compound as a yellow oil (3.7 g), t.l.c. (Toluene-ethanol-0.88 ammonia 80:20:2) Rf 0.62.

INTERMEDIATE 5

Methyl 5-[3-[[6-[[2-(4-amino-3,5-dichlorophenyl)-2-hydroxyethyl](phenylmethyl)amino]hexyl]oxy]-1-propynyl]-3-pyridinecarboxylate A suspension of Intermediate 2 (530 mg), methyl 5-bromo-3-pyridinecarboxylate (280 mg), BTPC (25 mg) and copper (I) iodide (2.5 mg) in triethylamine (5 ml, degassed by bubbling nitrogen through the solution, before addition of catalyst) was stirred under reflux under nitrogen for 2 h. The solvent was evaporated in vacuo and the residue was partitioned between water (25 ml) and ether (25 ml). The ethereal solution was washed with water and brine, dried and concentrated to give a brown oil which was purified by FCC eluting with hexane-ethyl acetate-triethylamine (80:20:1→50:50:1) to give the title compound as a yellow oil (450 mg), t.l.c. (Hexane-ethyl acetate-triethylamine 50:50:1) Rf 0.62.

INTERMEDIATE 6

4-Amino-α-[[[6-[[3-(6-amino-2-pyridinyl)-2-propynyl]oxy]hexyl](phenylmethyl)amino]methyl]-3,5-dichlorobenzenemethanol A solution of 2-amino-6-bromopyridine (2 g), Intermediate 2 (6.23 g), BTPC (100 mg) and copper (I) iodide (10 mg) in diethylamine (20 ml) and THF (20 ml) was stirred under nitrogen overnight. The solution was concentrated in vacuo to give a brown oil which was purified by FCC eluting with System A (98:2:1) to give the title compound as a brown oil (3.7 g), t.l.c. (Toluene-ethanol-0.88 ammonia 80:20:1), Rf 0.5.

INTERMEDIATE 7

2-[3-[[6-[[2-(4-Amino-3,5-dichlorophenyl)-2-hydroxyethyl](phenylmethyl)amino]hexyl]oxy]-1-propynyl]-N,N-diethyl-4-pyridinecarboxamide 2-Bromo-N,N-diethyl-4-pyridinecarboxamide (1.54 g) and Intermediate 2 (2.75 g) were treated as in Intermediate 6 to give the title compound as a brown oil (2.4 g), t.l.c. (System A 95:5:1) Rf 0.15.

INTERMEDATE 8

2-Bromo-N,N-diethyl-4-pyridinecarboxamide

Ethyl chloroformate (1.07 g) was added dropwise to a solution of 2-bromo-4-pyridinecarboxylic acid (2 g) and triethylamine (1 g) at 0°. The mixture was stirred at room temperature for 1 h, diethylamine (3 ml) was added dropwise and the resulting suspension was stirred vigorously for 2 h. The precipitate was collected by filtration and washed with water (20 ml) to give the title compound as a white solid (1.55 g), m.p. 200°–203°.

INTERMEDIATE 9

4-Amino-3,5-dichloro-α-[[[6-[[3-(6-dimethylamino-2-pyridinyl)-2-propynyl]oxy]hexyl](phenylmethyl)amino]methyl]benzenemethanol A solution of 2-bromo-6-dimethylaminopyridine (1.5 g), Intermediate 2 (4 g), BTPC (100 mg) and copper (I) iodide (10 mg) in triethylamine (20 ml) and THF (20 ml) was stirred at reflux under nitrogen overnight. The solution was concentrated in vacuo to give a brown oil which was purified by FCC eluting with hexane-ethyl acetate-triethylamine 90:10:→50:50:1) to give the title compound as a yellow oil (3 g), t.l.c. (Toluene-ethanol-0.88 ammonia 80:20:1) Rf 0.82.

INTERMEDIATE 10

N-[6-[3-[[6-[[2-(4-Amino-3,5-dichlorophenyl)-2-hydroxyethyl](phenylmethyl)amino]hexyl]oxy]-1-propynyl]-3-pyridinyl]acetamide A solution of N-(6-bromo-3-pyridinyl)acetamide (1.5 g), Intermediate 2 (3.7 g), BTPC (500 mg) and copper (I) iodide (50 mg) in triethylamine (20 ml) and acetonitrile (50 ml) was heated under reflux under nitrogen for 6 h. The solution was diluted with ether (100 ml), filtered and evaporated in vacuo to give an oil. Purification by FCC eluting with hexane:ethyl acetate (8:1→1:1) gave the title compound as a brown oil (2.3 g), t.l.c. (toluene-ethanol-0.88 ammonia, 80:20:1) Rf 0.49.

INTERMEDIATE 11

N-(6-Bromo-2-pyridinyl)methanesulphonamide

Methanesulphonyl chloride (0.74 g) in dichloromethane (5 ml) was added over 2 min to a stirred solution of 2-amino-6-bromopyridine (1.1 g) and pyridine (0.57 g) in dichloromethane (5 ml). After 4 h, the solvent was evaporated in vacuo to give an oil which was purified by FCC eluting with System A (95:5:1) to give the title compound as a white solid (1.2 g), m.p. 90°–94° C.

INTERMEDIATE 12

N-[6-[3-[[6-[[2-(4-Amino-3,5-dichlorophenyl)-2-hydroxyethyl](phenylmethyl)amino]hexyl]oxy]-1-propynyl]-2-pyridinyl]methanesulphonamide A mixture of N-(6-bromo-2-pyridinyl)methanesulphonamide (0.75 g), Intermediate 2 (1.6 g) BTPC (100 mg) and copper (I) iodide (10 mg) in diethylamine (25 ml) and THF (100 ml) was stirred at reflux for 4 h. The solution was concentrated in vacuo to give a brown oil which was purified by FCC eluting with System A (98:2:1→95:5:1) to give the title compound as a brown oil (1.2 g), t.l.c. (hexane-ethyl acetate-triethylamine 80:20:1) Rf 0.1.

INTERMEDIATE 13

5-[3-[[6-[[2-(4-Amino-3,5-dichlorophenyl)-2-hydroxyethyl]amino]hexyl]oxy]-1-propynyl]-N,N-diethyl-3-pyridinesulphonamide 5-Bromo-N,N-diethyl-3-pyridinesulphonamide (550 mg) and Intermediate 2 (974 mg) were treated as in Intermediate 12 to give, after FCC eluting with System A (98:2:1→95:5:1), the title compound as a yellow oil (450 mg) t.l.c. (toluene-ethanol-0.88 ammonia 80:20:1) Rf 0.8.

INTERMEDIATE 14

Methyl [(2-bromo-3-pyridinyl)oxy]acetate

To a solution of 2-bromo-3-pyridinol (5 g) in THF (100 ml) at 0° was added sodium hydride (1 g, 80% suspension in oil). The mixture was stirred under nitrogen for 30 min and methyl bromoacetate (3.26 ml) was added dropwise. The mixture was then heated under reflux for 2 h, poured into water (300 ml) and extracted with ethyl acetate (2×250 ml). The combined organic extracts were dried and concentrated to give a solid which was triturated with ether to give the title compound as a white solid (4.5 g), m.p. 63°-64° C.

INTERMEDIATE 15

[(2-Bromo-3-pyridinyl)oxy]acetic acid

Methyl [(2-bromo-3-pyridinyl)oxy]acetate (3 g) was stirred with 2N sodium hydroxide (30 ml) in methanol (30 ml) for 2 h. The solution was neutralised to pH 7 by portionwise addition of dowex (50) H+ methanol washed resin pH 7. The resin was filtered off, and the solution was concentrated in vacuo to give the title compound as a white solid (2.8 g), m.p. 172°-174°.

INTERMEDIATE 16

[(2-Bromo-3-pyridinyl)oxy]-N,N-diethylacetamide

Diethylamine (0.874 g) was slowly added with cooling to [(2-bromo-3-pyridinyl)oxy]acetic acid (2.58 g) in toluene (10 ml). The solution was then dded to phosphorous pentoxide (1.87 g) and diethylamine (1.74 g) in toluene (10 ml). After the addition the mixture was heated under reflux overnight. The dark solution was diluted with water (20 ml), made alkaline with 8% sodium bicarbonate (20 ml) and extracted with ethyl acetate (3×30 ml). The combined organic extracts were dried and the solvent was evaporated in vacuo to give the title compound as a brown oil (2.8 g). t.l.c. (toluene-ethanol-0.88 ammonia 80:20:1) Rf 0.47.

INTERMEDIATE 17

[[2-[3-[[6-[[2-(4-Amino-3,5-dichlorophenyl)-2-hydroxyethyl](phenylmethyl)amino]hexyl]oxy]-1-propynyl]-3-pyridinyl]oxy]-N,N-diethylacetamide A mixture of [(2-bromo-3-pyridinyl)oxy]-N,N-diethylacetamide (1.2 g), Intermediate 2 (2 g), BTPC (250 mg), copper (I) iodide (20 mg) in triethylamine (20 ml) and THF (30 ml) was stirred under reflux for 4 h. The solution was concentrated in vacuo to give a brown oil which was purified by FCC eluting with hexane-ethyl acetate-triethylamine 50:50:1→30:70:1) to give the title compound as a light brown oil (1.7 g), t.l.c. (toluene-ethanol-0.88 ammonia 80:20:1) Rf 0.47.

INTERMEDIATE 18

Methyl 5-[3-[[6-[[2-(4-amino-3,5-dichlorophenyl)-2-hydroxyethyl](phenylmethyl)amino]hexyl]oxy]-1-propynyl]-3-pyridineacetate A mixture of methyl 5-bromo-3-pyridineacetate (5 g), Intermediate 2 (10.74 g), BTPC (250 mg), copper (I) iodide (25 mg) in THF (30 ml) and diethylamine (20 ml) was stirred at reflux for 5 h. The solution was concentrated and partitioned between 8% sodium bicarbonate (70 ml) and ether (70 ml). The organic extract was dried and concentrated to give a black oil which was purified by FCC eluting with hexane-ethyl acetate-triethylamine (75:25:1) to give the title compound as a yellow oil (6.5 g), t.l.c. System A (95:5:1) Rf 0.5.

INTERMEDIATE 19

5-[3-[[6-[[2-(4-Amino-3,5-dichlorophenyl)-2-hydroxyethyl](phenylmethyl)amino]hexyl]oxy]-1-propynyl]-N,N-diethyl-3-pyridineacetamide A mixture of 5-bromo-N,N-diethyl-3-pyridineacetamide (1.23 g), Intermediate 2 (2.24 g), BTPC (100 mg) and copper (I) iodide (10 mg) in diethylamine (20 ml) and THF (20 ml) was stirred at reflux for 2 h. The solution was filtered and concentrated in vacuo to give a brown oil which was purified by FCC eluting with System A (95:5:1) to give the title compound as a yellow oil (1.7 g), t.l.c. (toluene-ethanol-0.88 ammonia, 80:20:1) Rf 0.6.

INTERMEDIATE 20

Methyl [[2-[3-[[6-[[2-(4-amino-3,5-dichlorophenyl)-2-hydroxyethyl](phenylmethyl)amino]hexyl]oxy]-1-propynyl]-3-pyridinyl]oxy]acetate A mixture of methyl [(2-bromo-3-pyridinyl)oxy]acetate (5 g), Intermediate 2 (10 g), BTPC (200 mg), copper (I) iodide (20 mg) in triethylamine (30 ml) and acetonitrile (330 ml) was stirred at room temperature overnight. The mixture was filtered and concentrated in vacuo to give a crude oil which was purified by FCC eluting with System A (98:2:1) to give the title compound as a brown oil (8 g), t.l.c. (System A 98:2:1) Rf 0.17.

INTERMEDIATE 21

1-Bromo-6-[(2-propynyl)oxy]hexane

A mixture of propargyl alcohol (5.6 g), 1,6-dibromohexane (73.2 g), tetrabutylammonium bisulphate (0.5 g), and aqueous sodium hydroxide (50%, w/v, 27 ml) was stirred at room temperature for 20 h, diluted with water (50 ml), and extracted with diethyl ether (2×100 ml). The dried extract was evaporated and the residue was purified on a column of silica (Merck 9385) eluting with cyclohexane followed by cyclohexane-diethyl ether (19:1) to give the title compound as a colourless oil (15.0 g), t.l.c. (cyclohexane-diethyl ether 9:1) Rf 0.4.

INTERMEDIATE 22

2-[3-[(6-Bromohexyl)oxy]-1-propynyl]-5-nitropyridine

2-Bromo-5-nitropyridine (6.4 g) and 1-bromo-6-[(2-propynyl)oxy]hexane (6.39 g) were treated as in Intermediate 20 to give, after FCC eluting with hexane-ether (2:1), the title compound as a brown oil (7 g), t.l.c. (hexane-ether 5:1) Rf 0.22.

INTERMEDIATE 23

2-[3-[(6-Bromohexyl)oxy]propyl]-5-nitropyridine

A mixture of 2-[3-[(6-bromohexyl)oxy]-1-propynyl]-5-nitropyridine (5 g) and dipotassium azodicarboxylate (30 g) in pyridine (200 ml) was stirred at room temperature, and acetic acid (18 ml) added. The mixture was stirred overnight and evaporated in vacuo to give a residue oil which was partitioned between 8% sodium bicarbonate (20 ml) and ethyl acetate (20 ml). The organic phase was dried and concentrated to give an oil which was purified by FCC eluting with hexane-ether (1:2→methanol) to give the title compound as an orange oil (300 mg), t.l.c. (toluene:ethanol 0.88 ammonia 80:20:1) Rf 0.75.

INTERMEDIATE 24

2-[6-[(6-Bromohexyl)oxy]-1-hexynyl]-4-pyridinecarboxamide

A mixture of 2-bromo-4-pyridinecarboxamide (1.1 g), BTPC (35 mg), copper (I) iodide (8 mg), 6-[(6-bromohexyl)oxy]-1-hexyne (1.43 g) and dicyclohexylamine (1.2 ml) in acetonitrile (20 ml) was stirred at room temperature, under nitrogen, for 20 h, then left to stand for 24 h. The yellow mixture was diluted with ether (50 ml), filtered, the filtrate dried and evaporated in vacuo to give a yellow waxy solid. The solid was purified by FCC eluting with System A (98:2:1) to give a pale yellow waxy solid. The solid was dissolved in ethanol:toluene (1:1), (20 ml) treated with activated charcoal (0.2 g), heated, filtered through hyflo and evaporated in vacuo to give the title compound as a pale yellow waxy solid (1.04 g), t.l.c. (toluene-ethanol: 0.880 ammonia, 90:10:1) Rf 0.31.

INTERMEDIATE 25

2-[6-[(6-Bromohexyl)oxy]hexyl]-4-pyridinecarboxamide

A solution of 2-[6-[(6-bromohexyl)oxy]-1-hexynyl]-4-pyridinecarboxamide (1.04 g) in ethanol (20 ml) was hydrogenated over pre-hydrogenated 10% palladium oxide on carbon (50% aqueous paste, 115 mg). The mixture was filtered through hyflo and the filtrate evaporated to give the title compound as a pale yellow solid (1.05 g), m.p. 73°–75°.

EXAMPLE 1

Methyl 5-[3-[[3-[[6-[[2-(4-amino-3,5-dichlorophenyl)-2-hydroxyethyl]amino]hexyl]oxy]propyl]-3-pyridinecarboxylate Methyl 5-[3-[[6-[[2-(4-amino-3,5-dichlorophenyl)-2-hydroxyethyl](phenylmethyl)amino]hexyl]oxy]-1-propynyl]-2-pyridinecarboxylate (8.0 g) was hydrogenated over pre-reduced palladium oxide on carbon (50% aqueous paste, 1.6 g) in ethanol (100 ml) containing hydrochloric acid (conc. HCl/ethanol, 1:9 v/v, 25 ml). The catalyst was removed by filtration through hyflo, the solvent was evaporated and the residual oil was partitioned between 8% sodium bicarbonate (100 ml) and ethyl acetate (100 ml). The organic layer was washed with water and brine, dried and concentrated to an oil which was purified by FCC eluting with System A (95:5:1) to give the title compound as a white solid (3.5 g), m.p. 84°–86°.

Analysis Found: C, 57.63; H, 6.67; N, 8.13; Cl, 13.57. $C_{24}H_{33}Cl_2N_3O_4$ requires C, 57.83; H, 6.67; N, 8.43; Cl, 14.23%. Examples 2-3 were prepared in a similar manner:

EXAMPLE 2

Ethyl 4-[3-[[6-[[2-(4-amino-3,5-dichlorophenyl)-2-hydroxyethyl]amino]hexyl]oxy]propyl]-2-pyridinecarboxylate From ethyl 4-[3-[[6-[[2-(4-amino-3,5-dichlorophenyl)-2-hydroxyethyl](phenylmethyl)amino]hexyl]oxy]-1-propynyl]-2-pyridinecarboxylate (3.5 g), gave, after trituration with ether, the title compound as a white solid (1.2 g), m.p. 68°–70°.

Analysis Found: C, 58.21; H, 6.88; N, 7.87; Cl, 14.07. $C_{25}H_{35}Cl_2N_3O_4$ requires C, 58.59; H, 6.88; N, 8.2; Cl, 13.84%.

EXAMPLE 3

4-Amino-α-[[[6-[3-(6-amino-2-pyridinyl)propoxy]hexyl]amino]methyl]-3,5-dichlorobenzenemethanol From 4-amino-α[[[6-[[3-(6-amino-2-pyridinyl)-2-propynyl]oxy]hexyl](phenylmethyl)amino]methyl]-3,5-dichlorobenzenemethanol (3.56 g), FCC eluting with System A (95:5:1→85:15:1) and trituration of the resulting yellow oil with ether gave the title compound as a white solid (1.7 g), m.p. 62°–65°, t.l.c. (Toluene-ethanol-0.88 ammonia 80:20:1) Rf 0.3.

EXAMPLE 4

2-[3-[[6-[[2-(4-Amino-3,5-dichlorophenyl)-2-hydroxyethyl]amino]hexyl]oxy]propyl]-4-pyridinecarboxamide (E)-butenedioate (2:1) (salt)

2-[3-[[6-[[2-(4-Amino-3,5-dichlorophenyl)-2-hydroxyethyl](phenylmethyl)amino]hexyl]oxy]-1-propynyl]-4-pyridinecarboxamide (1.8 g) was hydrogenated over pre-reduced palladium oxide on carbon (50% aqueous paste, 800 mg) in ethanol (30 ml) containing hydrochloric acid (conc. HCl/ethanol, 1:9 v/v, 9.54 ml). The catalyst was removed by filtration through hyflo, the solvent was evaporated and the residual oil was partitioned between 8% sodium bicarbonate (150 ml) and ethyl acetate (50 ml). The organic layer was washed with 8% sodium bicarbonate (50 ml), water (50 ml), and brine (50 ml), dried and concentrated to a brown oil which was purified by FCC eluting with System A (95:5:1) to give a pale yellow oil (0.79 g). A solution of the oil (0.77 g) and fumaric acid (95 mg) in methanol (10 ml) was concentrated to give an oil which was tritrated several times in ether to give a yellow gum. Two recrystallisations from isopropanol gave the title compound as a white solid (370 mg) m.p. 120°–125°. N.m.r. δ($CD_3OD$) 1.35–1.75, m, 8H —$CH_2$—($CH_2$)$_4$—$CH_2$—; 1.99, m, 2H, $OCH_2CH_2CH_3$-pyridyl; 2.90–3.15; m, >6H, —$CH_2NHCH_2$ plus —$CH_2$—pyridyl; 3.44, m, 4H, —$CH_2OCH_2$—; 4.80, dd, 1H, —CH(OH); 6.67, s, 1H, fumarate protons, 7.27, s, 2H, dichloroaniline CH; 7.63 (dd, 1H), 7.71 (s, 1H) and 8.57 (d, 1H), pyridyl CH.

Example 5 was prepared in a similar manner:

EXAMPLE 5

2-[3-[[6-[[2-(4-Amino-3,5-dichlorophenyl)-2-hydroxyethyl]amino]hexyl]oxy]propyl]-N,N-diethyl-4-pyridinecarboxamide (E)-butenedioate (2:1) salt From 2-[3-[[6-[[2-(4-amino-3,5-dichlorophenyl)-2-hydroxyethyl](phenylmethyl)amino]hexyl]oxy]-1-propynyl]-N,N-diethyl-4-pyridinecarboxamide (2.3 g). FCC eluting with System A (98:2:1) gave a yellow oil (0.72 g). Treatment of the oil (0.71 g) with fumaric acid in methanol gave, after trituration with ether, the title compound as a light yellow solid (580 mg) m.p. 92°–95°. N.m.r. δ (CH$_3$OD) 1.12 (t, 3H) and 1.25 (t, 3H), —N(CH$_2$CH$_3$)$_2$; 1.35–1.78, m, 8H, —CH$_2$—(CH$_2$—)$_4$—CH$_2$—; 1.97, m, 2H, —CH$_2$CH$_2$ pyridyl; 2.85–3.3, m, 8H, —CH$_2$NHCH$_2$— plus —CH$_2$OCH$_2$— plus —CH$_2$ pyridyl; 3.60–3.38, m, 6H, —CON(CH$_2$CH$_3$)$_2$ plus —OCH$_2$CH$_2$—; 4.82, dd, 1H, —CH(OH); 6.67, s, 1H, fumarate protons; 7.22 (dd, 1H), 7.27 (s, 3H) and 8.53 (d, 1H) dichloroaniline and pyridyl CH.

EXAMPLE 6

5-[3-[[6-[[2-(4-amino-3,5-dichlorophenyl)-2-hydroxyethyl]amino[hexyl]oxy]propyl]-3-pyridinecarboxylic acid A solution of methyl 5-[3-[[6-[[2-(4-amino-3,5-dichlorophenyl)-2-hydroxyethyl]amino]hexyl]oxy]propyl]-3-pyridinecarboxylate (1 g) in sodium hydroxide (10 ml) and ethanol (10 ml) was heated under reflux for 3 h. The solution was concentrated in vacuo and the aqueous layer was neutralised with hydrochloric acid (pH 7). The remaining precipitate was filtered off, washed with water (3×30 ml) and triturated in ether to give a yellow solid. The solid was treated with methanol, the insoluble inorganic material filtered off, and the solution evaporated in vacuo to give the title compound as a white solid (590 mg), m.p. 63°–68°, t.l.c. (Methanol-ether 1:1) Rf 0.65.

Example 7 was prepared in a similar manner:

EXAMPLE 7

2-[3-[[6-[[2-(4-amino-3,5-dichlorophenyl)-2-hydroxyethyl]amino]hexyl]oxy]propyl]-4-pyridinecarboxylic acid From ethyl 2-[3-[[6-[[2-(4-amino-3,5-dichlorophenyl)-2-hydroxyethyl]amino]hexyl]oxy]propyl]-4-pyridinecarboxylate (1.5 g), heating the reaction mixture under reflux for 2 days. The title compound was obtained as a pale yellow solid (270 mg), m.p. 69°–73°, t.l.c (Methanol-ether 1:1) Rf 0.5.

EXAMPLE 8

4-Amino-3,5-dichloro-α-[[[6-[3-(6-dimethylamino-2-pyridinyl)propoxy]hexyl]amino]methyl]benzenemethanol (E)-butenedioate (2:1) (salt)

Following the method of Example 4, but with omission of the final recrystallisations, 4-amino-3,5-dichloro-α-[[[6-[[3-(6-dimethylamino-2-pyridinyl)-2-propynyl]oxy]hexyl](phenylmethyl)amino]methyl]benzenemethanol (2.8 g) gave the title compound as a white solid (1.2 g), m.p. 105°–109°.

Analysis Found: C, 56.30; H, 6.99; N, 9.78; Cl, 12.12. C$_{24}$H$_{36}$Cl$_2$N$_4$O$_2$.0.5C$_4$H$_4$O$_4$.H$_2$O requires: C, 55.81; H, 7.21; N, 10.01; Cl, 12.67%.

EXAMPLE 9

N-[6-[3-[[6-[[2-(4-Amino-3,5-dichlorophenyl)-2-hydroxyethyl]amino]hexyl]oxy]propyl]-3-pyridinyl]acetamide A solution of N-[6-[3-[[6-[[2-(4-amino-3,5-dichlorophenyl)-2-hydroxyethyl](phenylmethyl)amino]hexyl]oxy]-1-propynyl]-3-pyridinyl]acetamide (1 g) was hydrogenated over palladium oxide on carbon (50% aqueous paste, 1 g) in ethanol (50 ml) containing hydrochloric acid for 24 h. The catalyst was removed by filtration through hyflo, the solvent was evaporated and the residual oil was partitioned between 8% sodium bicarbonate solution (150 ml) and ethyl acetate (150 ml). The combined organic extracts were dried and concentrated to give an oil. Purification by FCC eluting with System A (95:5:1) gave an oil which was triturated under ether (50 ml) to give the title compound as a white solid (250 mg) m.p. 66°–67°.

Analysis Found: C, 56.5; H, 7.0; N, 10.7; Cl, 14.3. C$_{24}$H$_{34}$Cl$_2$N$_4$O$_3$.0.5H$_2$O requires C, 56.9; H, 7.0; N, 11.1; Cl, 13.8%.

Examples 10–14 were prepared in a similar manner:

EXAMPLE 10

N-[6-[3-[[6-[[2-(4-Amino-3,5-dichlorophenyl)-2-hydroxyethyl]amino]hexyl]oxy]propyl]-2-pyridinyl]methanesulphonamide (E) butenedioate (2:1) (salt)

From N-[6[3-[[6-[[2-(4-amino-3,5-dichlorophenyl)-2-hydroxyethyl](phenylmethyl)amino]hexyl]oxy]-1-propynyl]-2-pyridinyl]methanesulphonamide (320 mg) gave, after FCC eluting with System A (98:2:1), a pale yellow oil. A solution of the oil (150 mg) with fumaric acid (16 mg) was concentrated to give an oil which was triturated several times in ether to give the title compound as a hemi-fumarate salt (130 mg), m.p. 62°–64° C.

Analysis Found: C, 49.57; H, 6.06; N, 8.62; Cl, 11.89; S, 4.95. C$_{23}$H$_{34}$Cl$_2$N$_4$O$_4$S.0.5.C$_4$H$_4$O$_4$ 1.1 mol H$_2$O requires C, 49.11; H, 6.3; N, 9.16; Cl, 11.60; S, 5.24.

EXAMPLE 11

5-[3-[[6-[[2-(4-Amino-3,5-dichlorophenyl)-2-hydroxyethyl]amino]hexyl]oxy]propyl]-N,N-diethyl-3-pyridinesulphonamide (E) butenedioate (2:1) (salt)

From 5-[3-[[6-[[2-(4-amino-3,5-dichlorophenyl)-2-hydroxyethyl](phenylmethyl)amino]hexyl]oxy]-1-propynyl]-N,N-diethyl-3-pyridinesulphonamide (300 mg) gave, after FCC eluting with System A (98:2:1), an oil (140 mg) which was treated in methanol with fumaric acid (15 mg), concentrated and the residue triturated under ether to give the title compound as a yellow solid (100 mg), m.p. 105°–106°.

Analysis Found: C, 52.65; H, 6.66; N, 8.39; Cl, 11.47, S, 4.68. C$_{28}$H$_{42}$Cl$_2$N$_4$O$_6$S 0.5 C$_4$H$_4$O$_4$ requires C, 53.08; H, 6.68; N, 8.84; Cl, 11.19; S, 5.06%.

EXAMPLE 12

3-[[2-[3-[[6-[[2-(4-Amino-3,5-dichlorophenyl)-2-hydroxyethyl]amino]hexyl]oxy]propyl]-3-pyridinyl]oxy]-N,N-diethylacetamide (E) butenedioate From [[2-[3-[[6-[[2-(4-amino-3,5-dichlorophenyl)-2-hydroxyethyl](phenylmethyl)amino]hexyl]oxy]-1-propynyl]-3-pyridinyl]oxy]-N,N-diethylacetamide (1.6 g) gave a yellow oil (710 mg) which was treated with fumaric acid (72 mg) in methanol (10 ml) and concentrated to give a gum which was triturated with hexane-ether (2:1) to give the title compound as a white solid (640 mg), m.p. 94°–95°.

Analysis Found: C, 57.1; H, 7.1; N, 8.7; Cl, 11.7; $C_{28}H_{24}Cl_2N_4O_4$ 0.5 $C_4H_4O_4$ requires C, 57.4; H, 7.1; N, 8.9; Cl, 11.3%.

EXAMPLE 13

Methyl 5-[3-[[6-[[2-(4-amino-3,5-dichlorophenyl)-2-hydroxyethyl)amino]hexyl]oxy]propyl]-3-pyridineacetate (E) butenedioate (2:1) (salt)

From methyl 5-[3-[[6-[[2-(4-amino-3,5-diichlorophenyl)-2-hydroxyethyl](phenylmethyl)amino]hexyl]oxy]-1-propynyl]-3-pyridineacetate (1.2 g) gave a yellow oil (470 mg). The oil in methanol (20 ml) was treated with fumaric acid (53 mg) and concentrated to give a gum which was triturated with ether to give the title compound as a white solid (480 mg), t.l.c. (toluene-ethanol-0.88 ammonia 80:20:1) Rf 0.56

Analysis Found: C, 52.94; H, 6.22; N, 6.50; Cl, 11.62. $C_{25}H_{35}Cl_2N_3O_4$.0.5 $C_4H_4O_4$ 2.2 $H_2O$ requires C, 53.15; H, 6.7; N, 6.89; Cl, 11.69%.

EXAMPLE 14

5-[3-[[6-[[2-(4-Amino-3,5-dichlorophenyl)-2-hydroxyethyl]amino]hexyl]oxy]propyl]-N,N-diethyl-3-pyridineacetamide (E) butenedioate (2:1) (salt)

From 5-[3- [[6-[[2-(4-amino-3,5-dichlorophenyl)-2-hydroxyethyl](phenylmethyl)amino]hexyl]oxy]-1-propynyl]-N,N-diethyl-3-pyridineacetamide (2:1) (salt) (1.7 g) gave, after FCC eluting with System A (99:1:1), a pale yellow oil A solution of the oil (580 mg) with fumaric acid (61 mg) in methanol was concentrated in vacuo to give an oil which was triturated several times in ether to give the title compound as a white solid (580 mg), m.p. 72°–75° C.

Analysis Found: C, 57.85; H, 7.11; N, 8.78; Cl, 11.46. $C_{28}H_{42}Cl_2N_4O_3$.0.5 $C_4H_4O_4$ 0.7 $H_2O$ requires C, 57.64; H, 7.34; N, 8.96; Cl, 11.34%

EXAMPLE 15

5-[3-[[6-[[2-(4-Amino-3,5-dichlorophenyl)-2-hydroxyethyl]amino]hexyl]oxy]propyl]-3-pyridineacetic acid A solution of methyl 5-[3-[[6-[[2-(4-amino-3,5-dichlorophenyl)-2-hydroxyethyl]amino]hexyl]oxy]propyl]-3-pyridineacetate (600 mg) in methanol (10 ml) and 2N sodium hydroxide (10 ml) was stirred at room temperature for 10 min. Dowex (50) H+ methanol washed resin was added portionwise until pH 7. The resin was filtered off, the solution concentrated in vacuo to give a brown solid which was triturated in ethanol/methanol (1:2) to give the title compound as a light brown solid (250 mg), m.p. 191°–192° t.l.c. (methanol) Rf 0.6.

EXAMPLE 16

5-[3-[[6-[[2-(4-Amino-3,5-dichlorophenyl)-2-hydroxyethyl]amino]hexyl]oxy]propyl]-3-pyridineethanol (E) butenedioate (2:1) (salt)

Methyl 5-[3-[[6-[[2-(4-amino-3,5-dichlorophenyl)-2-hydroxyethyl]amino]hexyl]oxy]propyl]-3-pyridineacetate (800 mg) in benzene (10 ml) was added dropwise to a stirred suspension of lithium aluminum hydride (95 mg) in ether (10 ml) at 0° C. The mixture was stirred overnight at room temperature under nitrogen, and more lithium aluminum hydride (40 mg) was added. After being stirred for a further 3 h, the mixture was treated with water (1 ml), followed by 2N sodium hydroxide (1 ml) and water (3 ml). The suspension was filtered through hyflo and washed with ethyl acetate (3×50 ml). The combined organic extracts were dried and concentrated to give a yellow oil which was purified by FCC eluting with System A (85:5:1) to give a yellow oil. The oil (450 mg), dissolved in methanol (10 ml), was treated with fumaric acid (52 mg) and concentrated to give an oil which was triturated with ether to give the title compound as a yellow solid (420 mg), m.p. 85°–86° C.

Analysis Found: C, 55.8; H, 6.9; N, 6.9; Cl, 12.4. $C_{24}H_{35}Cl_2N_3O_4$.0.5 $C_4H_4O_4.H_2O$ requires C, 55.7; H, 6.8; N, 7.4; Cl, 12.65%.

EXAMPLE 17

Methyl [[2-[3-[[6-[[2-(4-amino-3,5-dichlorophenyl)-2-hydroxyethyl]amino]hexyl]oxy]propyl]-3-pyridinyl]oxy]acetate (E)-butenedioate (2:1) (salt)

Methyl [[2-[3-[[6-[[2-(4-amino-3,5-dichlorophenyl)-2-hydroxyethyl](phenylmethyl)amino]hexyl]oxy]-1-propynyl]-3-pyridinyl]oxy]acetate (1.5 g ) was hydrogenated according to the method of Example 9 to give, after purification by FCC eluting with hexane-ethyl acetate-triethylamine (80:20:1) to give a yellow oil (600 mg). A portion of the oil (150 mg) in methanol (5 ml) was treated with fumaric acid (16 mg) and concentrated to give an oil which was triturated several times under ether to give the title compound as a white solid (120 mg), m.p. 84°–87°.

Analysis Found: C, 55.1; H, 6.3; N, 7.1; Cl 12.2. $C_{25}H_{35}Cl_2N_3O_5$.0.5 $C_4H_4O_4$ requires C, 55.3; H, 6.4; N, 7.2; Cl, 12.1%.

EXAMPLE 18

4-Amino-3,5-dichloro-α-[[[6-[3-[3-(2-hydroxyethoxy)-2-pyridinyl]propoxy]hexyl]amino]methyl]benzenemethanol (E) butenedioate (2:1) (salt)

Methyl [[2-[3-[[6-[[2-(4-amino-3,5-dichlorophenyl)-2-hydroxyethyl]amino]hexyl]oxy]propyl]-3-pyridinyloxy]acetate (400 mg) in ether (10 ml) was added dropwise to a stirred solution of lithium aluminum hydride (28 mg) in ether (5 ml) at 0° C. The mixture was stirred overnight at room temperature under nitrogen, water (0.5 ml) was added, followed by 2N sodium hydroxide (1.5 ml) and water (0.5 ml). The suspension was filtered through hyflo and washed with ethyl acetate (2×50 ml). Concentration of the filtrate gave an oil which was purified by FCC eluting with System A (95:5:1). The resulting oil (100 mg) was dissolved in methanol (2 ml) and treated with fumaric acid (12 mg). Concentration in vacuo gave an oil which was triturated several times under ether (3×10 ml) to give the title compound as a yellow solid (100 mg), m.p. 77°–80°.

Analysis Found: C, 54.24; H, 6.47; N, 6.94; Cl, 12.76. $C_{24}H_{35}Cl_2N_3O_4$.0.5$C_4H_4O_4$.0.75$H_2O$ requires C, 54.59; H, 6.78; N, 7.35; Cl, 12.4%.

EXAMPLE 19

4-Amino-3,5-dichloro-α-[[[6-[3-(5-nitro-2-pyridinyl)propoxy]hexyl]amino]methyl]benzenemethanol A solution of 4-amino-α-aminomethyl)-3,5-dichlorobenzenemethanol (361 mg), 2-[3-[(6-bromohexyl)oxy]propyl]-5-nitropyridine (378 mg) and N,N-diisopropylethylamine (168 mg) in dimethylformamide (5 ml) was stirred at 100° for 3 h. The solvent was evaporated in vacuo to give an oil. Purification by FCC eluting with System A (95:5:1) gave the title compound as a yellow solid (250 mg), m.p. 60°–61°.

Analysis Found: C, 53.6; H, 6.6; N, 11.4; Cl, 14.6; $C_{22}H_{30}Cl_2N_4O_4$. 0.2. $H_2O$ C, 54.0; H, 6.3; N, 11.4; cl, 14.5%.

EXAMPLE 20

2-[6-[[6-[[2-(4-Amino-3,5-dichlorophenyl)-2-hydroxyethyl]amino]hexyl]oxy]hexyl]-4-pyridinecarboxamide A mixture of 4-amino-α-(aminomethyl)-3,5-dichlorobenzenemethanol (0.87 g), 2-[6-[6-(bromohexyl)oxy]hexyl]-4-pyridinecarboxamide (1.05 g) and N,N-diisopropylethylamine (0.57 ml) was heated in N,N-dimethylformamide (30 ml) under nitrogen at 90° for 3 h, then left overnight at room temperature. The solvent was removed in vacuo and the residue purified by FCC eluting with toluene:ethanol:0.88 ammonia (90:10:1) to give the title compound as a white solid (0.6 g), m.p. 75°–78° (softens 65°).

Analysis Found: C, 59.35; H, 7.39; N, 10.41; Cl, 13.11. $C_{26}H_{38}Cl_2N_4O_3$ requires C, 59.42; H, 7.29; N, 10.66; Cl, 13.49%.

The following are examples of suitable formulations of compounds of the invention. The term 'active ingredient' is used herein to represent a compound of the invention.

| Tablets (Direct Compression) | |
|---|---|
| | mg/tablet |
| Active ingredient | 2.0 |
| Microcrystalline cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming maerials, such as hydroxypropylmethylcellulose, using standard techniques. Alternatively, the tablets may be sugar coated.

| Metered Dose Pressurised Aerosol (Suspension Aerosol) | | |
|---|---|---|
| | mg/metered dose | Per can |
| Active ingredient micronised | 0.100 | 26.40 mg |
| Oleic Acid BP | 0.100 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic is mixed with the trichloroflormethane at a temperature of 10°–15° C. and the micronised drug is mixed into the solution with a high shear mixer. The suspension is metered into aluminium aerosol cans and suitable metering valves delivering 85 mg of suspension are crimped onto the cans and the dichlorodifluoromethane is pressure filled into the cans through the valves.

| Inhalation Cartridges | |
|---|---|
| | mg/cartridge |
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents in the cartridges are administered using a powder inhaler such as the Glaxo Rotahaler.

I claim:
1. A Compound of formula (I)

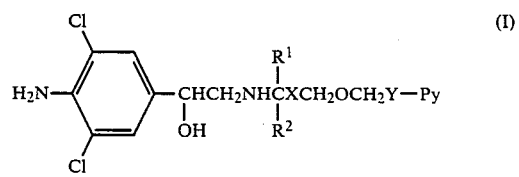

wherein

X represents a bond, or a $C_{1-6}$alkylene, $C_{2-6}$alkenylene or $C_{2-6}$alkynylene chain, and Y represents a bond, or a $C_{1-6}$alkylene, $C_{2-6}$alkenylene or $C_{2-6}$alkynylene chain with the proviso that the sum total of carbon atoms in X and Y is not more than 10;

$R^1$ and $R^2$ each represent a hydrogen atom or a $C_{1-3}$alkyl group, with the proviso that the sum total of carbon atoms in $R^1$ and $R^2$ is not more than 4; and Py represents a pyridyl group substituted by one or two substituents selected from nitro, $-(CH_2)_tR^3$, $-NR^4R^5$, $-(CH_2)_rSO_2NR^4R^5$, $-NR^6COR^3$, $-NR^6SO_2R^7$, $-(CH_2)_rCOR^3$, $-OCH_2COR^3$ and $-O(CH_2)_qR^3$; where $R^3$ represents a hydroxy, $C_{1-3}$alkoxy or $-NR^4R^5$ group;

$R^4$ and $R^5$ each represent a hydrogen atom or a $C_{1-4}$alkyl group;

$R^6$ represents a hydrogen atom or a $C_{1-4}$alkyl group;

$R^7$ represents a $C_{1-4}$alkyl, phenyl or $-NR^4R^5$ group;

q represents an integer 2 or 3;

r represents an integer from 0 to 3; and t represents an integer 1, 2 or 3;

or a physiologically acceptable salt or solvate thereof.

2. A compound according to claim 1 in which the sum total of carbon atoms in the chains X and Y is 4 to 9.

3. A compound according to claim 1 in which X is $-(CH_2)_3-$ or $-(CH_2)_4-$ and Y is $-CH_2-$, $-(CH_2)_2-$, $-(CH_2)_3-$ or $-(CH_2)_5-$ or X is $-(CH_2)_2C\equiv C-$ and Y is $-(CH_2)_2-$.

4. A compound according to claim 1 in which $R^1$ and $R^2$ are both hydrogen atoms, or $R^1$ is a hydrogen atom and $R^2$ is a $C_{1-3}$alkyl group.

5. A compound according to claim 1 in which Py is a pyridyl group substituted by nitro; amino; di($C_{1-4}$alkyl)amino; $-(CH_2)_rCOR^3$ where r is an integer from 0 to 3 and $R^3$ is a hydroxy, $C_{1-3}$alkoxy, amino or di($C_{1-4}$alkyl)amino group; $-(CH_2)_rSO_2NR^4R^5$ where r is an integer from 0 to 3 and $R^4$ and $R^5$ are $C_{1-4}$alkyl groups; $-NR^6COR^3$ where $R^6$ is a hydrogen atom and $R^3$ is a $C_{1-4}$alkyl group; $-NR^6SO_2R^7$ where $R^6$ is a hydrogen atom, and $R^7$ is a $C_{1-4}$alkyl group; $-(CH_2)_tR^3$ where t is an integer from 1 to 3 and $R^3$ is a hydroxy group; $-OCH-$ $_2COR^3$ where $R_3$ is a di($C_{1-4}$alkyl)amino or $C_{1-3}$alkoxy group; or —O(CH$_2$)$_q$R$^3$ where q is an integer 2 or 3 and R$^3$ is a hydroxy group.

6. A compound according to claim 1 in which R$^1$ represents a hydrogen atom and R$^2$ represents a methyl group or a hydrogen atom; the groups X and Y are both alkylene chains in which X is a C$_4$ alkylene chain and Y is a methylene, ethylene or pentylene chain; and Py represents a pyridyl group, attached to the rest of the molecule via the 2 or 3 position, and substituted by nitro; amino; dimethylamino; —(CH$_2$)$_r$COR$^3$ (where r is 0 or 1 and R$^3$ is methoxy, ethoxy, amino or dimethylamino); —SO$_2$N(C$_2$H$_5$)$_2$; —NHCOCH$_3$; —OCH$_2$COR$_3$ (where R$^3$ is —N(C$_2$H$_5$)$_2$ or methoxy); or —OCH$_2$CH$_2$OH; which are at the 3, 4, 5 or 6 position.

7. A compound selected from:
methyl 5-[3-[[6-[[2-(4-amino-3,5-dichlorophenyl)-2-hydroxyethyl]amino]hexyl]oxy]propyl]-3-pyridinecarboxylate;
2-[3-[[6-[[2-(4-amino-3,5-dichlorophenyl)-2-hydroxyethyl]amino]hexyl]oxy]propyl]-4-pyridinecarboxamide;
N-[6-[3-[[6-[[2-(4-amino-3,5-dichlorophenyl)-2-hydroxyethyl]amino]hexyl]oxy]propyl]-2-pyridinyl]methanesulphonamide;
2-[6-[[6-[[2-(4-amino-3,5-dichlorophenyl)-2-hydroxyethyl]amino]hexyl]oxy]hexyl]-4-pyridinecarboxamide;
and physiologically acceptable salts and solvates thereof.

8. A pharmaceutical composition for therapy or prophylaxis of a disease associated with reversible airways obstruction such as asthma or chronic bronchitis, which comprises an effective amount to alleviate said disease of at least one compound of formula

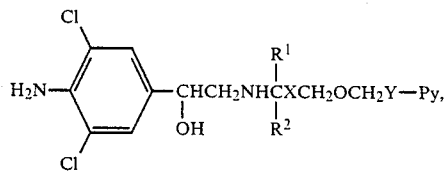

(I)

wherein
X represents a bond, or a C$_{1-6}$alkylene, C$_{2-6}$alkenylene or C$_{2-6}$alkynylene chain, and
Y represents a bond, or a C$_{1-6}$alkylene, C$_{2-6}$alkenylene or C$_{2-6}$alkynylene chain with the proviso that the sum total of carbon atoms in X and Y is not more than 10;
R$^1$ and R$^2$ each represent a hydrogen atom or a C$_{1-3}$alkyl group, with the proviso that the sum total of carbon atoms in R$^1$ and R$^2$ is not more than 4; and
Py represents a pyridyl group substituted by one or two substituents selected from nitro, —(CH$_2$)$_t$R$^3$, —NR$^4$R$^5$, —(CH$_2$)$_r$SO$_2$NR$^4$R$^5$, —NR$^6$COR$^3$, —NR$^6$SO$_2$R$^7$, —(CH$_2$)$_r$COR$^3$, —OCH$_2$COR$^3$ and —O(CH$_2$)$_q$R$^3$; where
R$^3$ represents a hydroxy, C$_{1-3}$alkoxy or —NR$^4$R$^5$ group;
R$^4$ and R$^5$ each represent a hydrogen atom or a C$_{1-4}$alkyl group;
R$^6$ represents a hydrogen atom or a C$_{1-4}$alkyl group;
R$^7$ represents a C$_{1-4}$alkyl, phenyl or —NR$^4$R$^5$ group;
q represents the integer 2 or 3;
r represents an integer from 0 to 3; and
t represents the integer 1, 2, or 3;
or a physiologically acceptable salt or solvate thereof, together with a physiologically acceptable carrier or excipient.

9. A method of therapy or prophylaxis of a disease associated with reversible airways obstruction such as asthma or chronic bronchitis in a patient which comprises administering to said patient an effective amount to alleviate said disease of a compound of formula

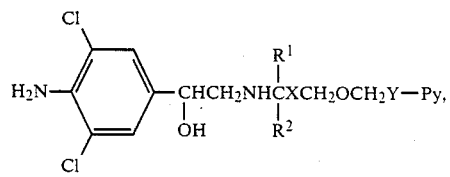

(I)

wherein
X represents a bond, or a C$_{1-6}$alkylene, C$_{2-6}$alkenylene or C$_{2-6}$alkynylene chain, and
Y represents a bond, or a C$_{1-6}$alkylene, C$_{2-6}$alkenylene or C$_{2-6}$alkynylene chain with the proviso that the sum total of carbon atoms in X and Y is not more than 10;
R$^1$ and R$^2$ each represent a hydrogen atom or a C$_{1-3}$alkyl group, with the proviso that the sum total of carbon atoms in R$^1$ and R$^2$ is not more than 4; and
Py represents a pyridyl group substituted by one or two substituents selected from nitro, —(CH$_2$)$_t$R$^3$, —NR$^4$R$^5$, —(CH$_2$)$_r$SO$_2$NR$^4$R$^5$, —NR$^6$COR$^3$, —NR$^6$SO$_2$R$^7$, —(CH$_2$)$_r$COR$^3$, —OCH$_2$COR$^3$ and —O(CH$_2$)$_q$R$^3$; where
R$^3$ represents a hydroxy, C$_{1-3}$alkoxy or —NR$^4$R$^5$ group;
R$^4$ and R$^5$ each represent a hydrogen atom or a C$_{1-4}$alkyl group;
R$^6$ represents a hydrogen atom or a C$_{1-4}$alkyl group;
R$^7$ represents a C$_{1-4}$alkyl, phenyl or —NR$^4$R$^5$ group;
q represents the integer 2 or 3;
r represents an integer from 0 to 3; and
t represents the integer 1, 2, or 3;
or a physiologically acceptable salt or solvate thereof.

* * * * *